US008688470B1

(12) United States Patent
Ambrose

(10) Patent No.: US 8,688,470 B1
(45) Date of Patent: Apr. 1, 2014

(54) LIABILITY INSURER AND HEALTH PLAN DATA EXCHANGE

(75) Inventor: Stephen Ambrose, Richmond, VA (US)

(73) Assignee: ICEX, Inc., Richmond, VA (US)

( * ) Notice: Subject to any disclaimer, the term of this patent is extended or adjusted under 35 U.S.C. 154(b) by 211 days.

(21) Appl. No.: 13/031,675

(22) Filed: Feb. 22, 2011

Related U.S. Application Data

(60) Provisional application No. 61/425,360, filed on Dec. 21, 2010.

(51) Int. Cl.
*G06Q 10/00* (2012.01)
*G06Q 50/00* (2012.01)

(52) U.S. Cl.
USPC .......................................................... 705/2

(58) Field of Classification Search
USPC ........................................................ 705/2, 3
See application file for complete search history.

(56) References Cited

U.S. PATENT DOCUMENTS

| | | | |
|---|---|---|---|
| 5,845,254 | A | 12/1998 | Lockwood et al. |
| 7,343,308 | B1 | 3/2008 | Rojewski et al. |
| 7,813,940 | B2 | 10/2010 | Ambrose |
| 7,840,422 | B1 | 11/2010 | Hail et al. |
| 7,962,385 | B2 | 6/2011 | Falk et al. |
| 7,970,632 | B2 * | 6/2011 | Ambrose ........................... 705/3 |
| 8,005,777 | B1 | 8/2011 | Owen et al. |
| 2002/0035528 | A1 * | 3/2002 | Simpson et al. ................ 705/35 |
| 2005/0010454 | A1 | 1/2005 | Falk et al. |
| 2005/0091080 | A1 | 4/2005 | Biats, Jr. |
| 2006/0116914 | A1 | 6/2006 | Stemple |
| 2007/0174094 | A1 | 7/2007 | Ramsey |
| 2007/0276704 | A1 | 11/2007 | Naumann et al. |
| 2007/0288272 | A1 | 12/2007 | Marks et al. |
| 2008/0172248 | A1 | 7/2008 | Ambrose |
| 2008/0172250 | A1 | 7/2008 | Ambrose |
| 2008/0249820 | A1 | 10/2008 | Pathria et al. |
| 2008/0275725 | A1 * | 11/2008 | Hach et al. ....................... 705/2 |
| 2008/0288282 | A1 | 11/2008 | Segal |
| 2009/0299764 | A1 * | 12/2009 | Ambrose ........................... 705/3 |
| 2009/0300065 | A1 | 12/2009 | Birchall |
| 2010/0049544 | A1 | 2/2010 | Ambrose |
| 2011/0022408 | A1 | 1/2011 | Pramik et al. |
| 2011/0077977 | A1 | 3/2011 | Collins et al. |

OTHER PUBLICATIONS http://www.mibsolutions.com/health, 18 pages, printed Mar. 28, 2012.
Brochure for www.mibsolutions.com/health, 8 pages, undated, downloaded on Mar. 28, 2012.
U.S. Appl. No. 13/658,104.
Brochure for Ingenix Medpoint Individual Health Profile, Copyright 2003, (6 pages).
U.S. Appl. No. 11/749,160.
U.S. Appl. No. 12/267,087.
U.S. Appl. No. 12/127,023.
U.S. Appl. No. 11/623,528.

* cited by examiner

*Primary Examiner* — Sheetal R Rangrej
*Assistant Examiner* — Trang Nguyen
(74) *Attorney, Agent, or Firm* — DLA Piper LLP US

(57) ABSTRACT

A data information exchange, which accesses data from liability insurers and health plans, manages the data and allows health plans to identify when their plan participants are third party claimants in injury claims. In another aspect, subrogation entities access the data information exchange in order to perform subrogation operations for the health plans, relating to the health plan's participants. In another aspect, coordination of benefit recovery entities access the data information exchange in order to perform recovery operations for the health plans, relating to health providers which rendered services to participants of the health plans.

66 Claims, 5 Drawing Sheets

LIABILITY INSURER AND HEALTH PLAN DATA EXCHANGE

RELATED U.S. APPLICATION DATA

This application claims the benefit of U.S. Provisional Application No. 61/425,360, filed on Dec. 21, 2010 now abandoned.

BACKGROUND

Health plans use of number of cost containment tools in their daily operations, including TPL (third party liability) identification, coordination of benefits (COB) and subrogation.

The first tool is known as TPL identification. This is when a health plan including its contracted vendors utilize health claims data and other plan participant information to determine if the participant is a third party claimant in an injury claim, and if the participant received a settlement from an insurer or defendant.

Identifying TPL cases is highly dependent on a number of factors, which traditionally make it more of a best guess than a knowledge-based operation. Generally, it consists of two parts.

First, health plans and their vendors frequently data mine submitted health provider claims, looking for particular diagnosis and procedure codes, which have a possibility of indicating an accident or injury situation relating to the provider services rendered to the plan participant.

The provider claim data does indicate when the individual receiving care has sought health care services as a result of an auto accident, work-related injury or "other accident". However, these choices do not necessarily indicate fault, nor do they indicate whether or not the health plan's participant has or will file an injury claim against a responsible party.

Additionally, many types of injury claims, such as those relating to professional and product liability, as well as wrongful death, are generally not well identified by health claims data alone.

Many injury claims are settled without going to court; therefore, such information is kept privately between claimant, their attorney and the responsible party, which is typically a liability insurer of self-pay defendant.

The second part in identifying TPL situations is when health plans and vendors, upon establishing a reasonable "hunch" from the data mined claim information, send out generic accident questionnaires to their selected plan participants.

These form letters rely squarely on the plan participant to admit to having an injury where another party was involved, as well as volunteer their choice to be involved in an injury claim. Once answered accurately, these questionnaires are sent back to the health plan or its vendor, thereby allowing the plan to stake a financial claim to a portion of monies paid from an injury claim settlement, to the plan participant.

Such surveys are notoriously ineffective because participants can answer "no" when asked if a third party was involved because they believe that answering "yes" could lead to an investigation or further involvement on their part.

If an injury claim is accurately identified by the participant's response, the second tool a health plan uses is a follow-up action known as health care subrogation. This is the health plan's right to pursue any course of action, in its own name or the name of its self-insured client, against a third party who is liable for a loss which has been paid by the plan. If a settlement has been paid by the health plan to the participant, the health plan stakes a subrogation claim against the participant directly.

A third tool is also a follow-up action to TPL identification; it is known as Coordination of Benefits (COB). COB is used by health plans to halt and if necessary, recover current health claim payments from contracted health care providers, when such claim payments have been or are related to a TPL circumstance.

Additionally, subrogation and COB have time factors, where the sooner a plan knows about a TPL applicable to its plan participant, the better chance it may have to recover its full stake of overpaid monies owed. For this reason, accuracy plus speed are vital components of identification and cost containment operations.

These and other known drawbacks exist in the area of third party liability (TPL) identification and related cost containment operations.

BRIEF DESCRIPTION OF THE SEVERAL VIEWS OF THE DRAWINGS

The embodiments will become more readily appreciated as the same become better understood by reference to the following illustrations.

DETAILED DESCRIPTION OF SEVERAL EMBODIMENTS

Embodiments of the present invention relate to a computer-based information exchange, which may receive data records from both a liability insurer and a health plan, stores the data, compares both sets of data records to each other, may create a matched data record that identifies an individual as both a third party claimant and a participant of the health plan, and thereafter, may distribute the matched data to the health plan. The system and process have several embodiments, where the matched data may be distributed to the health plan.

One embodiment illustrates the matched data distributed to the health plan for no consideration or value.

Another embodiment illustrates the matched data distributed to the health plan, after the health plan agrees to assign cost containment operations, relating to its plan participants within the matched data to a recovery entity, wherein the recovery entity may have a financial relationship to the computer-based information exchange.

Another embodiment illustrates the matched data distributed to the health plan, after the health plan agrees to assign cost containment operations, relating to those health providers that furnished services to the health plan's participants within the matched data to a recovery entity, wherein the recovery entity may have a financial relationship to the computer-based information exchange.

Another embodiment illustrates the matched data distributed to the health plan, after the health plan may agree to pay a fee to the computer-based information exchange, where the fee relates to the value of the matched data.

Figure 1:
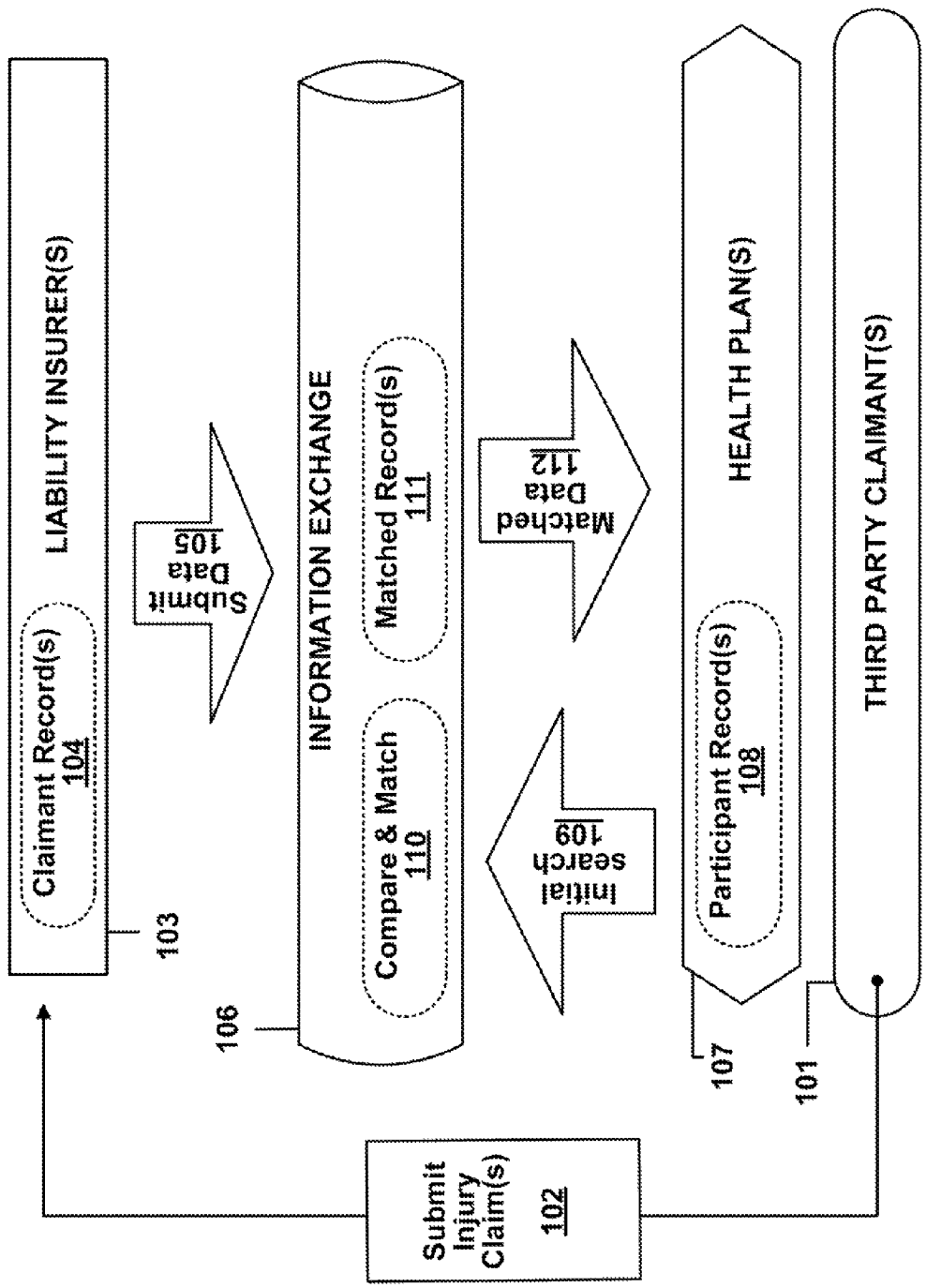
FIG. 1 is a schematic block diagram illustrating one of the embodiments, where liability insurers supply third party claimant data through a computer-based data exchange and to health plans of claimants.

In FIG. 1, an illustration related to one of the embodiments illustrates third party claimants 101 who submit injury claim 102 to liability insurers 103, where the liability insurers represent defendant parties having causal relationships to the third party claimants' injuries.

After receiving the third party claimants' injury claims, the liability insurers 103 create injured claimant data records 104, which may consist of the third party claimants' first names, last names, dates of birth social security numbers, home addresses, dates of injuries and the names, addresses, phone and fax numbers of applicable attorneys, which represent the third party claimants.

In 105, the liability insurers submit injured claimant data records to a computer-based information exchange 106. The injured claimant data records may be in a flat file format, such as Excel® or .CSV files, but the file format may not necessarily be limited as such.

The computer-based information exchange 106 may be comprised of a server, personal computer, or other computing device capable of executing software applications. As a non-limiting illustrative example, the computer-based information exchange 106 may comprise a server or group of servers, which may be or include, for instance, a workstation running Microsoft Windows™ NT™, Microsoft Windows™ 2000, Unix, Linux, Xenix, IBM, AIX™, Hewlett-Packard UX™, Novell Netware™, Sun Microsystems Solaris™, OS/2™, BeOS™, Mach, Apache, OpenStep™ or other operating system or platform.

The injured claimant data records sent in 105 may be accepted by and stored within the information exchange's database. The injured claimant data records may be added to other injured claimant data records from the same and other liability insurers.

The database of the information exchange may be or include, for instance an Oracle™ relational database sold commercially by Oracle Corporation. Other databases, such as Informix™, DB2 (Database 2) or other data storage or query formats, platforms, or resources such as OLAP (On Line Analytical Processing), SQL (Standard Query Language), a SAN (storage area network), Microsoft Access™ or others may also be used, incorporated, or accessed into the computer-based information exchange of 106.

Health plans 107 create plan participant data records 108, which may consist of the plan participants' first names, last names, dates of birth, social security numbers and home addresses.

In 109, health plans 107 may perform searches for their plan participants, who are also third party claimants stored in the computer-based information exchange 106. The health plans may search by submitting the plan participant data records 108 to the computer-based information exchange 106. The plan participant data records may be in a flat file format, such as Excel® or .CSV files, but the file format may not be necessarily limited as such.

In 110 the computer-based information exchange may compare common headings and data entries of the plan participant data records received in 109 to all the existing, stored injured claimant data records it has in its database.

When there are matches between common headings and data of both record types, the computer-based information exchange in 111 may create matched data records. The matched data records may contain the common first names, last names, dates of birth, social security numbers and home addresses of individuals who are both third party claimants and participants of the health plans.

Also included in the matched data records of 111 may be individuals' injury dates and if applicable, the names, addresses, phone and fax numbers of attorneys representing the third party claimants.

In 112, the health plans 107 may download the matched data records 111 from the computer-based information exchange 106.

Figure 2:
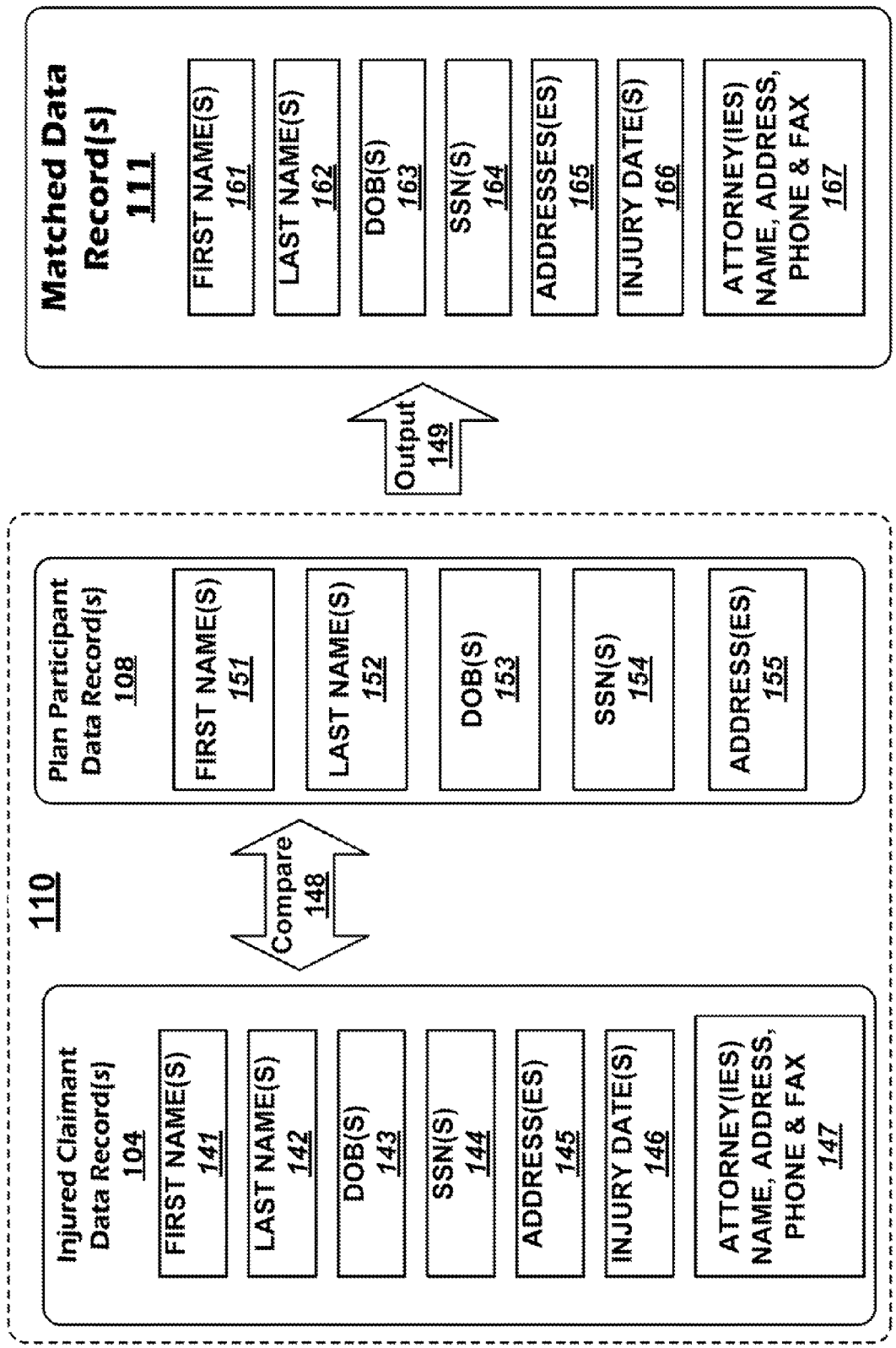
FIG. 2 is a flow diagram expanding the 'compare and match' operation of the 'information exchange' portion in the embodiment.

In FIG. 2, the compare and match function of the computer-based information exchange 110 of FIG. 1 is shown in an exploded view, demonstrating the compare and match function, common in all of the embodiments.

Within the compare and match function 110, the injured claimant data records 104 may consist of the third party claimants' first names 141, last names 142, dates of birth 143, social security numbers 144, home addresses 145, dates of injuries 146 and the name, address, phone and fax numbers of any applicable attorneys, which represent the third party claimants 147.

Also within the compare and match function 110, the plan participant data records 108 may consist of the plan participants' first names 151, last names 152, dates of birth 153, social security numbers 154 and home addresses 155.

In 148 both the injured claimant and plan participant data records are compared to each other. When there is a match between common headings and data of both record types 149, there is matched data record 111 created.

The matched data records may contain the common first names 161, last names 162, dates of birth 163, social security numbers 164 and home addresses 165 of individuals who are both a third party claimant and a participant of the health plan.

Also included in the matched data records of 111 may be the individuals' injury dates 166 and if applicable, the representing attorney's name, address, phone and fax numbers 167.

Figure 3:
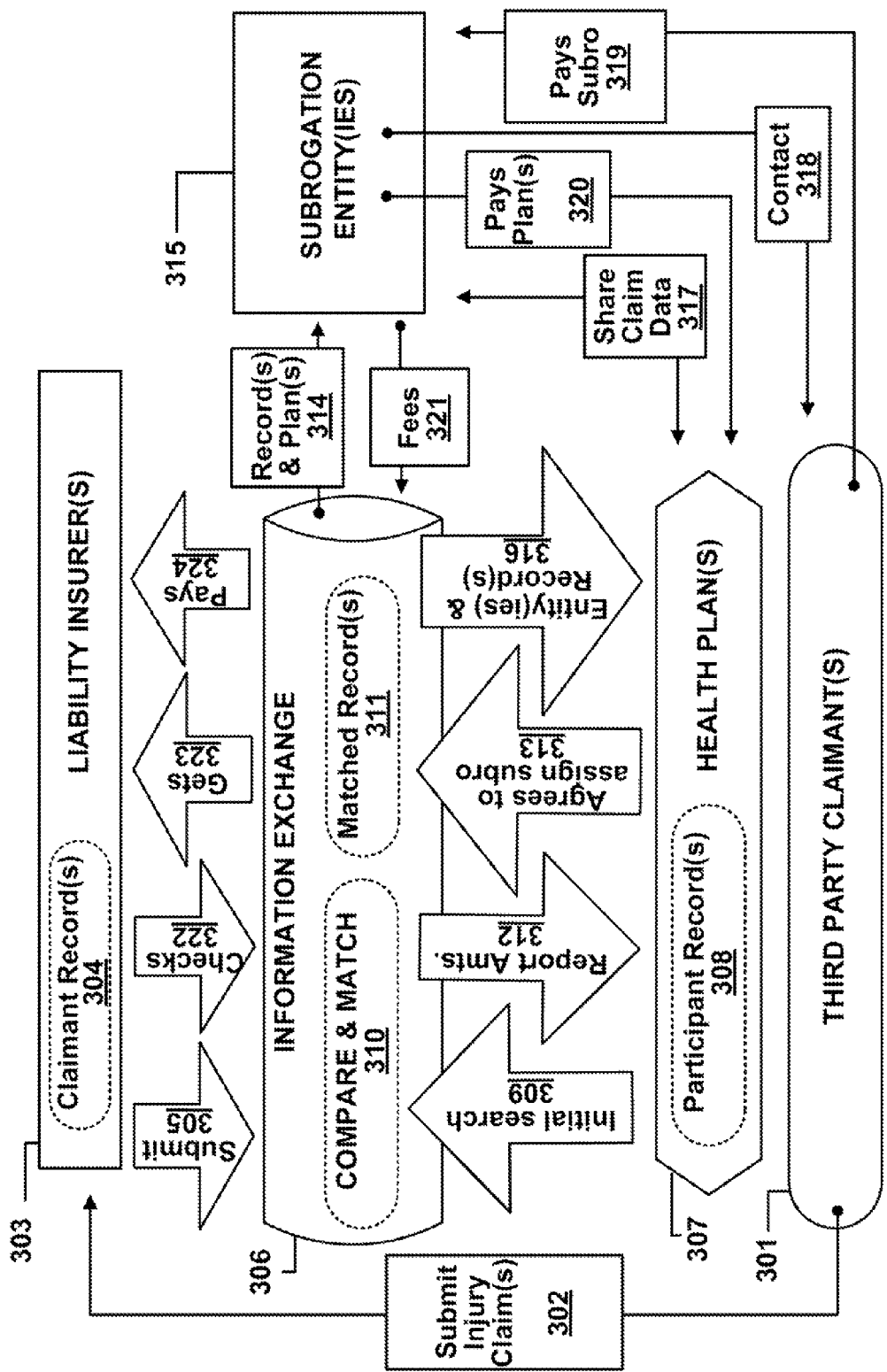
FIG. 3 is a schematic block diagram illustrating another of the embodiments, where health plans assign their cost containment operations, relating to recovery from their plan participants, to recovery entities.

In FIG. 3, another embodiment illustrates third party claimants 301 who submit injury claim 302 to liability insurers 303, where the liability insurers may represent defendant parties having causal relationships to injuries sustained by third party claimants.

After receiving the third party claimants' injury claims, the liability insurers 303 create injured claimant data records 304, which may consist of the third party claimants' first names, last names, dates of birth social security numbers, home addresses, dates of injuries and the names, addresses, phone and fax numbers of applicable attorneys, which represent the third party claimants.

In 305, the liability insurers submit the injured claimant data records to a computer-based information exchange 306. The injured claimant data records may be in a flat file format, such as Excel® or .CSV files, but the file format may not necessarily be limited as such.

The computer-based information exchange 306 may be comprised of a server, personal computer, or other computing device capable of executing software applications. As a non-limiting illustrative example, the computer-based information exchange 306 may comprise a server or group of servers, which may be or include, for instance, a workstation running Microsoft Windows™ NT™, Microsoft Windows™ 2000, Unix, Linux, Xenix, IBM, AIX™, Hewlett-Packard UX™, Novell Netware™, Sun Microsystems Solaris™, OS/2™, BeOS™, Mach, Apache, OpenStep™ or other operating system or platform.

The injured claimant data records sent in 305 may be accepted by and stored within the information exchange's database. The injured claimant data records may be added to other injured claimant data records from the same and other liability insurers.

The database of the information exchange may be or include, for instance an Oracle™ relational database sold commercially by Oracle Corporation. Other databases, such as Informix™, DB2 (Database 2) or other data storage or query formats, platforms, or resources such as OLAP (On Line Analytical Processing), SQL (Standard Query Language), a SAN (storage area network), Microsoft Access™ or others may also be used, incorporated, or accessed into the computer-based information exchange of 306.

Health plans 307 create plan participant data records 308, which may consist of the plan participants' first names, last names, dates of birth, social security numbers and home addresses.

In 309, the health plans 307 may search for any their plan participants, who are also third party claimants stored in the computer-based information exchange 306. The health plans may search by submitting plan participant data records 308 to the computer-based information exchange 306. The plan participant data records may be in a flat file format, such as Excel® or .CSV files, but the file format may not necessarily be limited as such.

In 310 the computer-based information exchange may compare common headings and data entries of plan participant data records received in 309 to all the existing, stored injured claimant data records it has in its database.

When there are matches between common headings and data of both injured claimant and plan participant data records, the computer-based information exchange in 311 may create matched data records. The matched data records may contain the common first names, last names, dates of birth, social security numbers and home addresses of individuals who are both third party claimants and participants of the health plans.

Also included in the matched data records of 311 may be the individuals' injury dates and if applicable, the representing attorneys' names, addresses, phone and fax numbers.

In 312, the computer-based information exchange may submit the number of individuals within the matched data records 311, but may not reveal any identifying information in the matched data records to the health plans 307.

In 313, the health plans 307 may agree to assign subrogation operations, relating to their plan participants within the matched data records 311 to recovery entities providing health plan subrogation services ("subrogation entity") 315. The subrogation entities may have a financial relationship to the computer-based information exchange 306.

After the health plans agree to assign subrogation services, in 314 the computer-based information exchange 306 may submit the matched data records and the names of third party claimants' health plans 307 to the subrogation entities 315.

In 316, the health plans 307 may download the matched data records 311 and the names of the subrogation entities 315 assigned to handle the subrogation operations pertaining to the health plans' participants within the matched data records, wherein the downloads come from the computer-based information exchange 3-6.

In 317, the subrogation entities 315 may contact the health plans 307; the health plans share health claim data with the subrogation entities, relevant to the health plans' participants and dates of the plan participants' injuries in the matched claim records 311.

Thereafter, in 318, the subrogation entities 315 may contact the third party claimants 301, who are also plan participants of the health plans 307. Later, in 319 the third party claimants 301 pay on subrogation claims, the payments made to the subrogation entities 315.

After subrogation monies have been collected, in 320 the subrogation entities 315 may make portioned payments to the health plans 307. After such payments to the health plans, the subrogation entities may keep a portion of remaining subrogation monies, remitting the remaining monies thereafter, through fee payments 321 to the computer-based information exchange 306.

At this time, the liability insurers 303 may be permitted to perform status checks 322 on the third party claimants within the injured claimant data records 304 that the liability insurers submitted to the computer-based information exchange in 305.

In response to the status checks 322, the computer-based information exchange 306 sends the liability insurers 303 back status responses 323.

In 324, after the computer-based information exchange 306 receives its fee 321 from subrogation entities 315, the computer-based information exchange may remit a portion of its fee payments to the liability insurers 303.

Figure 4:
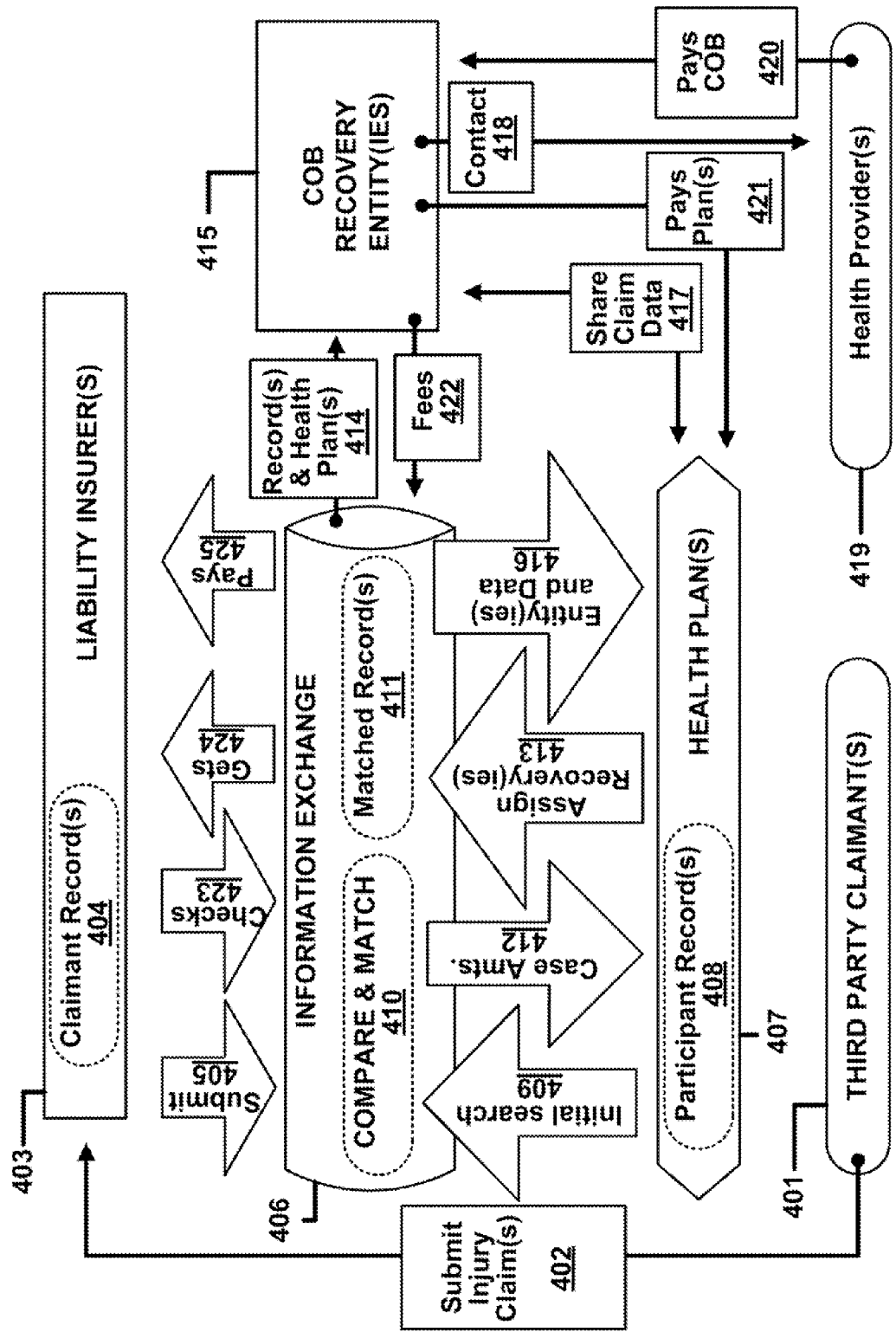
FIG. 4 is a schematic block diagram illustrating an example of another embodiment, where health plans assign their cost containment operations, relating to recovery from health providers, to Coordination of Benefit (COB) recovery entities.

In FIG. 4, another embodiment illustrates third party claimants 401 who may submit injury claim 402 to liability insurers 403, where the liability insurers represent defendant parties having causal relationships to injuries sustained by third party claimants.

After receiving the third party claimants' injury claims, the liability insurers 403 may create injured claimant data records 404, which may consist of the third party claimants' first names, last names, dates of birth social security numbers, home addresses, dates of injuries and the names, addresses, phone and fax numbers of applicable attorneys, which represent the third party claimants.

In 405, the liability insurers may submit the injured claimant data records to a computer-based information exchange 406. The injured claimant data records may be in a flat file format, such as Excel® or .CSV files, but the file format may not necessarily be limited as such.

The computer-based information exchange 406 may be comprised of a server, personal computer, or other computing device capable of executing software applications. As a non-limiting illustrative example, the computer-based information exchange 406 may comprise a server or group of servers, which may be or include, for instance, a workstation running Microsoft Windows™ NT™, Microsoft Windows™ 2000, Unix, Linux, Xenix, IBM, AIX™, Hewlett-Packard UX™, Novell Netware™, Sun Microsystems Solaris™, OS/2™, BeOS™, Mach, Apache, OpenStep™ or other operating system or platform.

The injured claimant data records sent in 405 may be accepted by and stored within the information exchange's database. The injured claimant data records may be added to other injured claimant data records from the same and other liability insurers.

The database of the information exchange may be or include, for instance an Oracle™ relational database sold commercially by Oracle Corporation. Other databases, such as Informix™, DB2 (Database 2) or other data storage or query formats, platforms, or resources such as OLAP (On Line Analytical Processing), SQL (Standard Query Language), a SAN (storage area network), Microsoft Access™ or others may also be used, incorporated, or accessed into the computer-based information exchange of 406.

Health plans 407 create plan participant data records 408, consisting of the plan participants' first names, last names, dates of birth, social security numbers and home addresses.

In 409, the health plans 407 search for any their plan participants, who are also third party claimants stored in the computer-based information exchange 406. The health plans search by submitting plan participant data records 408 to the computer-based information exchange 406. The plan participant data records may be in a flat file format, such as Excel® or .CSV files, but the file format may not be necessarily limited as such.

In 410 the computer-based information exchange may compare common headings and data entries of plan participant data records received in 409 to all the existing, stored injured claimant data records it has in its database.

When there are matches between common headings and data of both injured claimant and plan participant data records, the computer-based information exchange in 411 may create matched data records. The matched data records may contain the common first names, last names, dates of birth, social security numbers and home addresses of individuals who are both third party claimants and participants of the health plans.

Also included in the matched data records of 411 may be the individuals' injury dates and if applicable, the representing attorneys', names, addresses, phone and fax numbers.

In 412, the computer-based information exchange submits the number of individuals within the matched data records 411, but may not reveal any identifying information in the matched data records to the health plans 407.

In 413, the health plans 407 may agree to assign (Coordination of Benefits) COB recovery operations, relating to the health providers 419 who provided services to the health plans' participants within the matched data records 411 to recovery entities providing COB services ("COB recovery entities") 415. The COB recovery entities may have a financial relationship to the computer-based information exchange 406.

After the health plans agree to assign the COB recovery services, in 414 the computer-based information exchange 406 may submit the matched data records and the names of the third party claimants' health plans to the COB recovery entities 415.

In 416, the health plans 407 may download the matched data records 411 and the names of the COB recover entities 415 assigned to handle the COB recovery operations pertaining to the health plans' participants within the matched data records, wherein the downloads come from the computer-based information exchange 406.

In 417, the COB recovery entities 415 may contact the health plans 407; the health plans may share health claim data with the COB recovery entities, including the names of the health providers 419 who rendered care to the plan participants, relevant to the dates of the plan participants' injuries in the matched claim records 411.

Thereafter, in 418, the COB recovery entities 415 may contact the rendering health care providers 419. Later, in 420 the health providers 419 may pay on COB recovery claims to the COB recovery entities 415.

After COB recovery monies have been collected, in 421 the COB recovery entities 415 may make portioned payments to the health plans 407. After such payments to the health plans, the COB recovery entities may keep portions of remaining COB recovery monies, remitting the remaining monies thereafter, through fee payments 422 to the computer-based information exchange 406.

At this time, the liability insurers 403 may be permitted to perform status checks 423 on the third party claimants within the injured claimant data records 404, submitted by the liability insurers to the computer-based information exchange in 405.

In response to the status checks 423, the computer-based information exchange 406 sends the liability insurers 403 back status responses 424.

In 425, after the computer-based information exchange 406 receives fees 422 from COB recovery entities 415, the computer-based information exchange may remit portions of its fee payments to the liability insurers 403.

Figure 5:
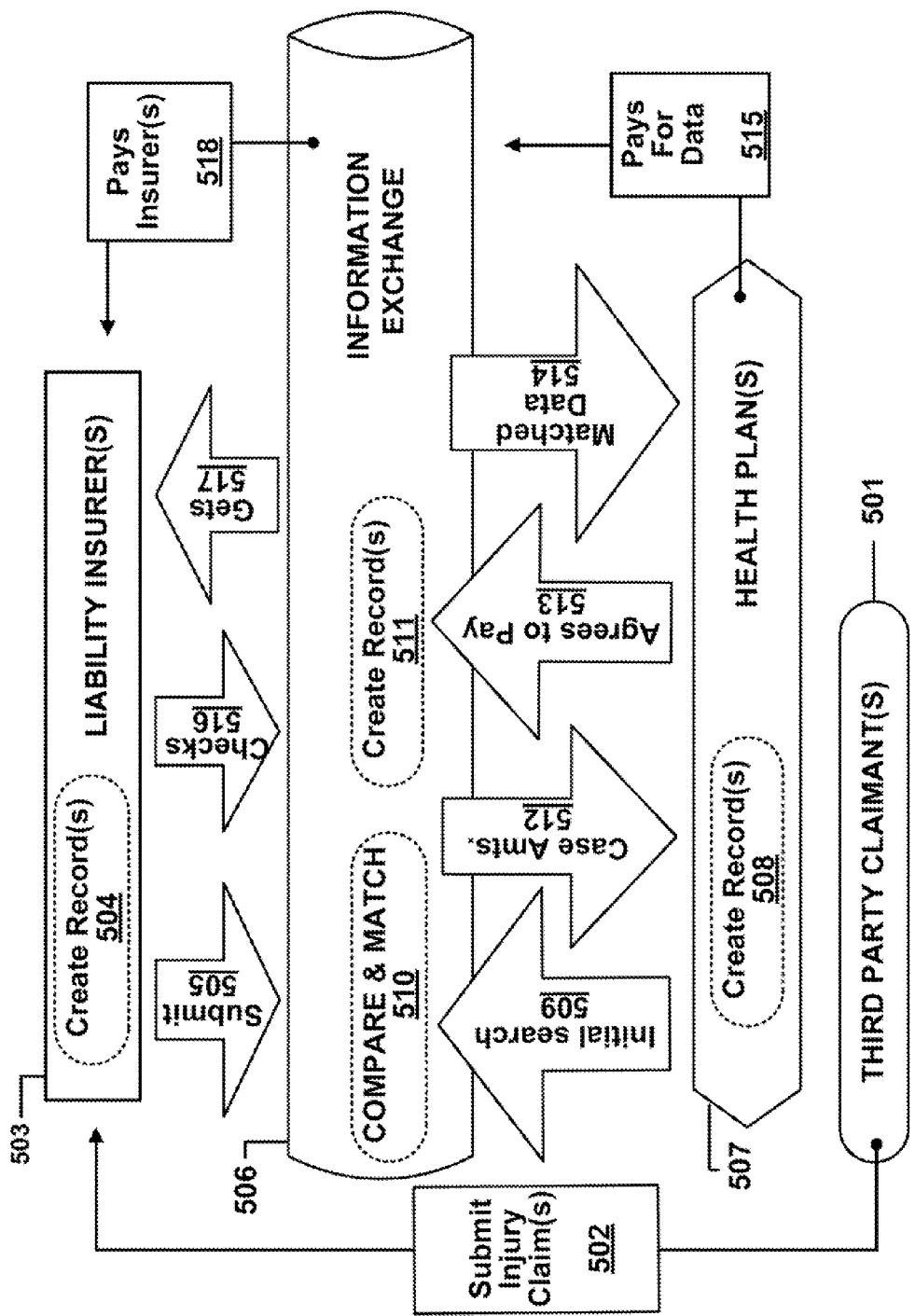
FIG. 5 is a variation relating to one of the embodiments, where health plans, for consideration and value, agree to make payments to the information exchange, in order to receive matched data.

In FIG. 5, an illustration related to one of the embodiments illustrates third party claimants 501 who may submit injury claim 502 to liability insurers 503, where the liability insurers may represent defendant parties having causal relationships to the third party claimants' injuries.

After receiving the third party claimants' injury claims, the liability insurers 503 may create injured claimant data records 504, which may consist of the third party claimants' first names, last names, dates of birth social security numbers, home addresses, dates of injuries and the names, addresses, phone and fax numbers of applicable attorneys, which represent the third party claimants.

In 505, the liability insurers may submit injured claimant data records to a computer-based information exchange 506. The injured claimant data records may be in a flat file format, such as Excel® or .CSV files, but the file format may not necessarily be limited as such.

The computer-based information exchange 506 may be comprised of a server, personal computer, or other computing device capable of executing software applications. As a non-limiting illustrative example, the computer-based information exchange 506 may comprise a server or group of servers, which may be or include, for instance, a workstation running Microsoft Windows™ NT™, Microsoft Windows™ 2000, Unix, Linux, Xenix, IBM, AIX™, Hewlett-Packard UX™, Novell Netware™, Sun Microsystems Solaris™, OS/2™, BeOS™, Mach, Apache, OpenStep™ or other operating system or platform.

The injured claimant data records sent in 505 may be accepted by and stored within the information exchange's database. The injured claimant data records may be added to other injured claimant data records from the same and other liability insurers.

The database of the information exchange may be or include, for instance an Oracle™ relational database sold commercially by Oracle Corporation. Other databases, such as Informix™, DB2 (Database 2) or other data storage or query formats, platforms, or resources such as OLAP (On Line Analytical Processing), SQL (Standard Query Language), a SAN (storage area network), Microsoft Access™ or others may also be used, incorporated, or accessed into the computer-based information exchange of 506.

Health plans 507 may create plan participant data records 508 consisting of the plan participants' first names, last names, dates of birth, social security numbers and home addresses.

In 509, health plans 507 may perform searches for their plan participants, who are also third party claimants stored in the computer-based information exchange 506. The health plans search by submitting the plan participant data records 508 to the computer-based information exchange 506. The plan participant data records may be in a flat file format, such as Excel® or .CSV files, but the file format may not necessarily be limited as such.

In 510 the computer-based information exchange may compare common headings and data entries of the plan participant data records received in 509 to all the existing, stored injured claimant data records it has in its database.

When there are matches between common headings and data of both record types, the computer-based information exchange in 511 creates matched data records. The matched data records may contain the common first names, last names, dates of birth, social security numbers and home addresses of individuals who are both third party claimants and participants of the health plans.

Also included in the matched data records of 511 may be individuals' injury dates and if applicable, the names, addresses, phone and fax numbers of attorneys representing the third party claimants.

In 512, the computer-based information exchange may submit the number of individuals within the matched data records 511, but may not reveal any identifying information in the matched data records to the health plans 507.

In 513, the health plan 507 agrees to pay the computer-based information exchange 506 a fee in exchange for the health plan downloading matched data record 511.

Thereafter, in 514 the health plan 507 downloads the matched data record 511 from the computer-based information exchange 506. Later, in 515, the health plan 507 may pay the computer-based information exchange 506, in consideration for the downloaded data, as agreed upon in 513.

At this time, the liability insurer 503 may be permitted to perform a status check 516 on the third party claimants within the injured claimant data record 504 it submitted to the computer-based information exchange in 505.

In response to the status check 516, the computer-based information exchange 506 sends the liability insurer 503 back a status response 517.

In 518, after the computer-based information exchange 506 receives its fee 515 from health plan 507, the computer-based information exchange may remit a portion of its fee payment to the liability insurer 503.

Similarly, it is envisioned that singular elements may also be interpreted as one or more.

What is claimed is:

1. A system for an information exchange process comprising:
    a hardware processor configured for:
    i) performing processing associated with comparing health plan member data records to injured claimant data records from a liability insurer, utilizing a compare and match component of a computer-based information exchange system, the injured claimant data records stored in an information exchange database in communication with a processor, the injured claimant data records containing information about injured party claimants, the information comprising: demographic data of the injured claimants, applicable legal representatives of the injured claimants, type of claim filed, date of loss or accident, or date of claim filing to the liability insurer, or any combination thereof, the injured claimant data records created by the liability insurer after receiving injury claims from injured party claimants, the health plan member data records not derived from medical claim data comprising treatment data, diagnosis date, or medication data, or any combination thereof, and containing identifying demographic information about members of health plans, the health plan member data records created by the health plans;
    ii) performing processing associated with creating a matched data record by creating a query file from the health plan member data records used to query the injured claimant data records stored in the information exchange data base and transforming the query file and the injured claimant data records into a matched data record that identifies, utilizing the compare and match component of the computer-based information exchange system, a match of the identifying demographic information shared between injured claimant data records and the health plan member data records, the matched data record indicating individuals who are both injured party claimants and members of the health plan information about the injury claims relating to the members of the health plan, and the matched data record being stored in a matched records database; and
    iii) performing processing associated with making available the matched data records so that information related to the filing of an actual injury claim is accessible to the health plan for purposes of health plan subrogation.

2. The system of claim 1, where the processor is further configured for performing processing associated with sending the matched data records to the health plans.

3. The system of claim 1, where the injured party claimants are represented by legal agents, the legal agents comprising:
    i) an individual attorney;
    ii) a legal firm;
    iii) a legal association;
    iv) public aid;
    v) a mediation firm;
    vi) a consultant;
    vii) a parent; or
    viii) a legal guardian; or
    ix) any combination of the above.

4. The system of claim 1, where the liability insurer comprises coverage for the following lines of business:
    i) personal
    ii) commercial;
    iii) specialty;
    iv) reinsurance; or
    v) any line of business where received claims include medical billings received for injuries and treatment related to the claims; or
    vi) any combination of the above.

5. The system of claim 1, where health plans are health insurance coverage plans comprising:
    i) Medicaid;
    ii) self-insured health plans;
    iii) group health plans;
    iv) individual health plans;
    v) county health plans;
    vi) state health plans;
    vii) federal health plans;
    viii) private union health plans;
    ix) workers compensation plans;
    x) medical riders on, liability insurance plans; or
    xi) vendors of health plans; or
    xii) any combination of the above.

6. The system of claim 1, where injury claims are based upon circumstances, the circumstances comprising:
    i) vehicular accident;
    ii) work-related;
    iii) premise liability;
    iv) inadequate security;
    v) construction site;

vi) amusement park;
vii) sexual misconduct;
viii) occupational disease;
ix) defective product;
x) pharmaceutical-related;
xi) birth injury;
xii) assault;
xiii) police brutality;
xiv) slip;
xv) fall;
xvi) negligence;
xvii) wrongful death;
xviii) medical malpractice; or
xix) any causal circumstance which contributes, in part or whole, to an injury claim; or
xx) any combination of the above.

7. The system of claim 1, where injured claimant data records are records comprising:
i) the first names of injured party claimants;
ii) the last names of injured party claimants;
iii) the birth dates of injured party claimants;
iv) the social security numbers of injured party claimants;
v) the home addresses of injured party claimants;
vi) the dates the injured party claimants filed their injury claims;
vii) the dates the liability insurers received the injury claims;
viii) the names of the attorneys representing the injured party claimants;
ix) the addresses of the attorneys representing the injured party claimants;
x) the phone numbers of the attorneys representing the injured party claimants;
xi) the fax numbers of the attorneys representing the injured party claimants; or
xii) the mails of the attorneys representing the injured party claimants; or
xiii) any combination of the above.

8. The system of claim 7, where social security numbers of injured party claimants comprise truncated portions of social security numbers.

9. The system of claim 1, where health plan member data records are records comprising:
i) the first names of members of health plans;
ii) the last names of members of health plans;
iii) the birth dates of members of health plans;
iv) the social security numbers of members of health plans; or
v) the home addresses of members of health plans; or
vi) any combination of the above.

10. The system of claim 9, where social security numbers of health plan members comprise truncated portions of social security numbers.

11. The system of claim 1, where health plan member data records comprise the names of the health plans.

12. The system of claim 1, where injury claims comprise lawsuits.

13. The system of claim 1, where the processor is further configured for performing processing associated with health plans making payments to the entity operating the information exchange process, in consideration and value for receiving matched data records.

14. The system of claim 13, where the processor is further configured for performing processing associated with paying a portion of collected health plan payments to liability insurers.

15. The system of claim 1, where the processor is further configured for performing processing associated with sending the matched data records to subrogation vendors.

16. The system of claim 1, where an entity that performs processing also performs subrogation operations on behalf of the health plans.

17. The system of claim 16, where the processor is further configured for performing processing associated with submitting subrogation claims against injury claim settlements of injured party claimants who are also health plan members, the subrogation claims submitted on behalf of the health plans.

18. The system of claim 16, where the processor is further configured for performing processing associated with calculating portions payable to the health plans after receiving subrogation payments out of injury claim settlements.

19. The system of claim 16, where the processor is further configured for performing processing associated with calculating portions payable to the computer-based information exchange after receiving subrogation payments from injury claim settlements.

20. The system of claim 16, where the processor is further configured for performing processing associated with calculating portions payable to liability insurers after receiving subrogation payments from injury claim settlements.

21. The system of claim 16, where the processor is further configured for performing processing associated with calculating the owed subrogation claim monies from injury claim settlements of health plan members who are also injured party claimants.

22. The system of claim 1, where the processor is further configured for performing processing associated with sending the matched data records to coordination of benefit recovery vendors.

23. The system of claim 1, where an entity that performs processing also performs coordination of benefit recovery operations on behalf of the health plans.

24. The system of claim 23, where the processor is further configured for performing processing associated with calculating owed coordination of benefit recovery claim monies.

25. The system of claim 23, where the processor is further configured for performing processing associated with recovering coordination of benefit monies on behalf of the health plans.

26. The system of claim 23, where the processor is further configured for performing processing associated with calculating portions of the recovered coordination of benefit monies payable to the health plans after receiving coordination of benefit recovery payments.

27. The system of claim 23, where the processor is further configured for performing processing associated with calculating portions payable to the computer-based information exchange after receiving coordination of benefit recovery payments.

28. The system of claim 23, where the processor is further configured for performing processing associated with calculating portions payable to liability insurers after receiving coordination of benefit recovery payments.

29. The system of claim 1, where the matched data reports identify liability insurers involved in the injury claims to the health plans which receive the reports.

30. The system of claim 1, where injured party claimants are third party claimants.

31. The system of claim 1, wherein the liability insurer provides coverage for casualty claims.

32. The system of claim 1, wherein the liability insurer provides coverage for workers compensation claims.

33. The system of claim 1, wherein the liability insurer provides coverage including:
   i) product liability;
   ii) general liability;
   iii) public liability; or
   iv) professional liability; or
   v) any combination thereof.

34. A method for an information exchange process comprising:
   i) performing processing associated with comparing health plan member data records to injured claimant data records from a liability insurer, utilizing a compare and match component of a computer-based information exchange system in communication with a processor circuit in communication with a database, the injured claimant data records stored in an information exchange database in communication with a processor, the injured claimant data records containing information about injured party claimants, the information comprising: demographic data of the injured claimants, applicable legal representatives of the injured claimants, type of claim filed, date of loss or accident, or date of claim filing to the liability insurer, or any combination thereof, the injured claimant data records created by the liability insurer after receiving injury claims from injured party claimants, the health plan member data records not derived from medical claim data comprising treatment data, diagnosis data, or medication data, or any combination thereof, and containing identifying demographic information about members of health plans, the health plan member data records created by the health plans;
   ii) performing processing associated with creating a matched data record by creating a query file from the health plan member data records used to query the injured claimant data records stored in the information exchange data base and transforming the query file and the injured claimant data records into a matched data record that identifies, utilizing the compare and match component of the computer-based information exchange system, a match of the identifying demographic information shared between injured claimant data records and the health plan member data records, the matched data record indicating individuals who are both injured party claimants and members of the health plan information about the injury claims relating to the members of the health plan, and the matched data record being stored in a matched records database; and
   iii) performing processing associated with making available the matched data records so that information related to the filing of an actual injury claim is accessible to the health plan for purposes of health plan subrogation.

35. The method of claim 34, further comprising performing processing associated with sending the matched data records to the health plans.

36. The method of claim 34, wherein the injured party claimants are represented by legal agents, the legal agents comprising:
   i) an individual attorney;
   ii) a legal firm;
   iii) a legal association;
   iv) public aid;
   v) a mediation firm;
   vi) a consultant;
   vii) a parent; or
   viii) a legal guardian; or
   ix) any combination of the above.

37. The method of claim 34, where a liability insurer is an insurer handling lines of business, the lines of business comprising:
   i) personal
   ii) commercial;
   iii) specialty;
   iv) reinsurance; or
   v) any line of business where received claims include medical billings received for injuries and treatment related to the claims; or
   vi) any combination of the above.

38. The method of claim 34, wherein health plans are health insurance coverage plans comprising:
   i) Medicaid;
   ii) self-insured health plans;
   iii) group health plans;
   iv) individual health plans;
   v) county health plans;
   vi) state health plans;
   vii) federal health plans;
   viii) private union health plans;
   ix) workers compensation plans;
   x) medical riders on liability insurance plans; or
   xi) vendors of health plans; or
   xii) any combination of the above.

39. The method of claim 34, where injury claims are based upon circumstances, the circumstances comprising:
   i) vehicular accident;
   ii) work-related;
   iii) premise liability;
   iv) inadequate security;
   v) construction site;
   vi) amusement park;
   vii) sexual misconduct;
   viii) occupational disease;
   ix) defective product;
   x) pharmaceutical-related;
   xi) birth injury;
   xii) assault;
   xiii) police brutality;
   xiv) slip;
   xv) fall;
   xvi) negligence;
   xvii) wrongful death;
   xviii) medical malpractice; or
   xix) any causal circumstance which contributes, in part or whole, to an injury claim; or
   xx) any combination of the above.

40. The method of claim 34, where injured claimant data records are records comprising:
   i) the first names of injured party claimants;
   ii) the last names of injured party claimants;
   iii) the birth dates of injured party claimants;
   iv) the social security numbers of injured party claimants;
   v) the home addresses of injured party claimants;
   vi) the dates the injured party claimants filed their injury claims;
   vii) the dates the liability insurer received the injury claims;
   viii) the names of the attorneys representing the injured party claimants;
   ix) the addresses of the attorneys representing the injured party claimants;
   x) the phone numbers of the attorneys representing the injured party claimants;
   xi) the fax numbers of the attorneys representing the injured party claimants; or xii) the entails of the attorneys representing the injured party claimants; or xiii) any combination of the above.

41. The method of claim 34, where health plan member data records are records comprising:

i) the first names of members of health plans;

ii) the last names of members of health plans;

iii) the birth dates of members of health plans;

iv) the social security numbers of members of health plans; or v) the home addresses of members of health plans; or vi) any combination of the above.

42. The method of claim 41, where social security numbers of injured party claimants comprise truncated portions of social security numbers.

43. The method of claim 41, where social security numbers of health plan members comprise truncated portions of social security numbers.

44. The method of claim 34, where health plan member data records comprise the names of the health plans.

45. The method of claim 34, where injury claims comprise lawsuits.

46. The method of claim 34, further comprising performing processing associated with health plans making payments to the entity operating the information exchange process, in consideration and value for receiving matched data records.

47. The method of claim 46, further comprising performing processing associated with paying a portion of collected health plan payments to liability insurers.

48. The method of claim 34, further comprising performing processing associated with sending the matched data records to subrogation vendors.

49. The method of claim 34, wherein an entity that performs processing also performs subrogation operations on behalf of the health plans.

50. The method of claim 49, further comprising performing processing associated with calculating the owed subrogation claim monies from injury claim settlements of health plan members who are also injured party claimants.

51. The method of claim 34, further comprising performing processing associated with sending the matched data records to coordination of benefit recovery vendors.

52. The method of claim 34, where an entity that performs processing also performs coordination of benefit recovery operations on behalf of the health plans.

53. The method of claim 52, further comprising performing processing associated with calculating owed coordination of benefit recovery claim monies.

54. The method of claim 52, further comprising performing processing associated with recovering coordination of benefit monies on behalf of the health plans.

55. The method of claim 52, further comprising performing processing associated with calculating portions of the recovered coordination of benefit monies payable to the health plans after receiving coordination of benefit recovery payments.

56. The method of claim 52, further comprising performing processing associated with calculating portions payable to the computer-based information exchange after receiving coordination of benefit recovery payments.

57. The method of claim 52, further comprising performing processing associated with calculating portions payable to liability insurers after receiving coordination of benefit recovery payments.

58. The method of claim 49, further comprising performing processing associated with submitting subrogation claims against injury claim settlements of injured party claimants who are also health plan members, the subrogation claims submitted on behalf of the health plans.

59. The method of claim 49, further comprising performing processing associated with calculating portions payable to the health plans after receiving subrogation payments out of injury claim settlements.

60. The method of claim 49, further comprising performing processing associated with calculating portions payable to the computer-based information exchange after receiving subrogation payments from injury claim settlements.

61. The method of claim 49, further comprising performing processing associated with calculating portions payable to liability insurers after receiving subrogation payments from injury claim settlements.

62. The method of claim 34, where the matched data reports identify liability insurers involved in the injury claims to the health plans which receive the reports.

63. The method of claim 34, where injured party claimants are third party claimants.

64. The method of claim 34, wherein the liability insurer provides coverage for casualty claims.

65. The method of claim 34, wherein the liability insurer provides coverage for workers compensation claims.

66. The method of claim 34, wherein the liability insurer provides coverage including:

i) product liability;

ii) general liability;

iii) public liability; or iv) professional liability; or v) any combination thereof.

\* \* \* \* \*